（12) United States Patent
Tachibana et al.

(10) Patent No.: US 6,387,044 B1
(45) Date of Patent: May 14, 2002

(54) LAPAROSCOPE APPARATUS

(75) Inventors: Akifumi Tachibana; Ryuichiro Niizeki; Masaya Tatsumi, all of Kyoto (JP)

(73) Assignee: J. Morita Manufacturing Corporation, Kyoto (JP)

(*) Notice: Subject to any disclaimer, the term of this patent is extended or adjusted under 35 U.S.C. 154(b) by 0 days.

(21) Appl. No.: 09/452,504

(22) Filed: Dec. 1, 1999

(30) Foreign Application Priority Data

Dec. 2, 1998 (JP) .......................................... 10-342667
Apr. 7, 1999 (JP) .......................................... 11-099855

(51) Int. Cl.$^7$ ................................................ A61B 1/00
(52) U.S. Cl. ..................... 600/114; 600/121; 600/138; 600/177
(58) Field of Search ................................ 600/114, 121, 600/138, 176, 177

(56) References Cited

U.S. PATENT DOCUMENTS

| 4,610,242 A | * | 9/1986 | Santangelo et al. | 600/114 |
| 5,184,602 A | * | 2/1993 | Anapliotis et al. | 600/176 |
| 5,278,642 A | * | 1/1994 | Danna et al. | 600/181 |
| 5,369,525 A | * | 11/1994 | Bala et al. | 359/435 |
| 5,817,015 A | * | 10/1998 | Adair | 600/121 |
| 6,120,434 A | * | 9/2000 | Kimura et al. | 600/114 |

* cited by examiner

Primary Examiner—John Mulcahy
(74) Attorney, Agent, or Firm—Koda & Androlia

(57) ABSTRACT

A laparoscope apparatus for use in laparoscopic surgery or the like comprises a cannula with an inner hollow having therein a light guide for introducing light to its tip end for illuminating the object to be observed, and an endoscope which is capable of being pulled into and out from the inner hollow of the cannula. The cannula is airtightly sealed with a transparent member at its tip end, while the endoscope has therein an image pick-up with a wide-angle lens, and the image pick-up is housed in the cannula close to the transparent member.

6 Claims, 12 Drawing Sheets

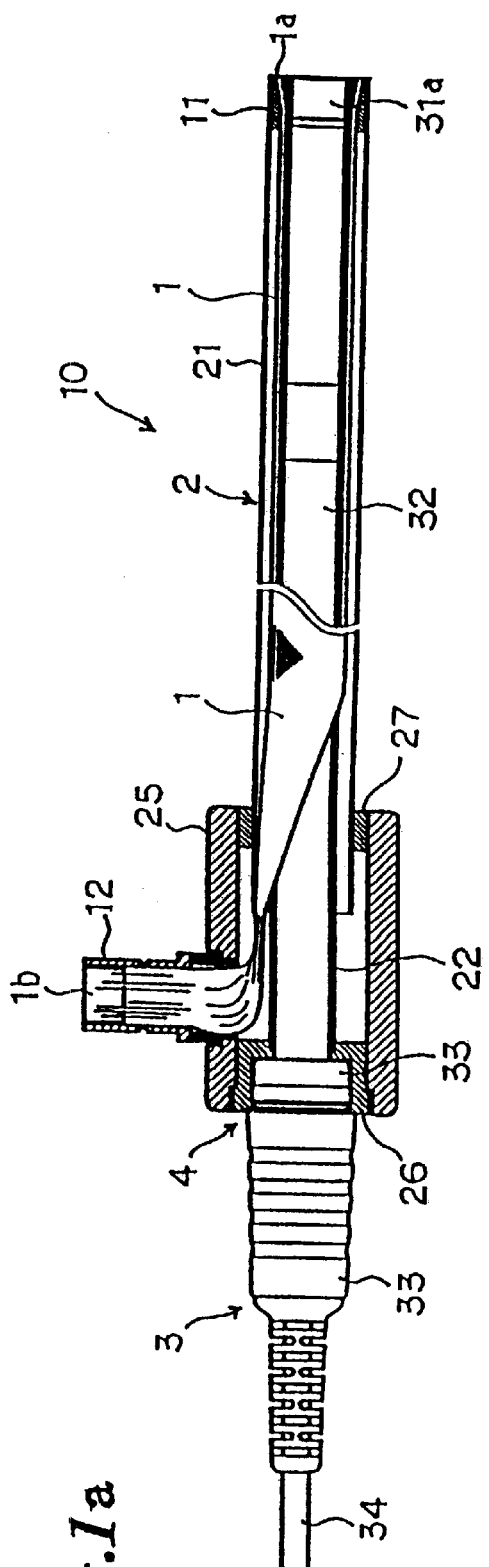
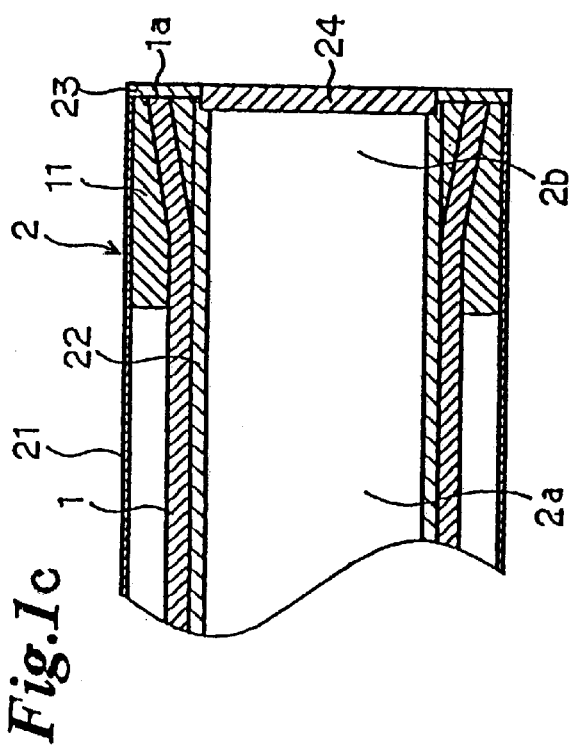
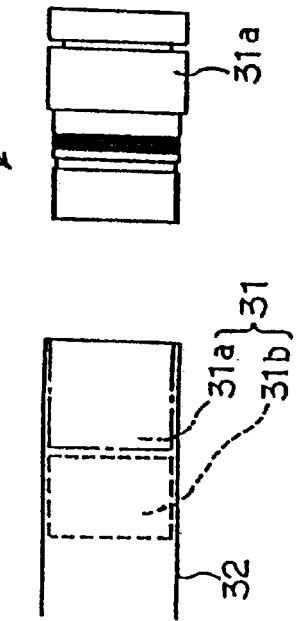
Fig.1a
Fig.1b
Fig.1c

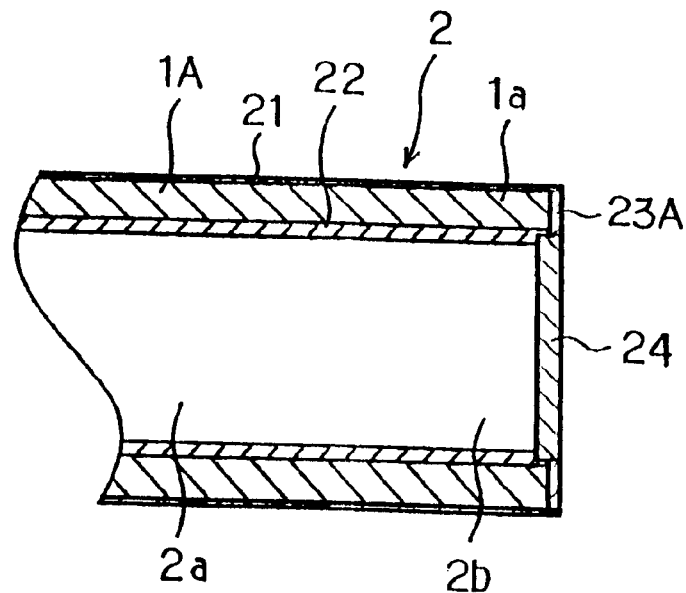
*Fig.2* a
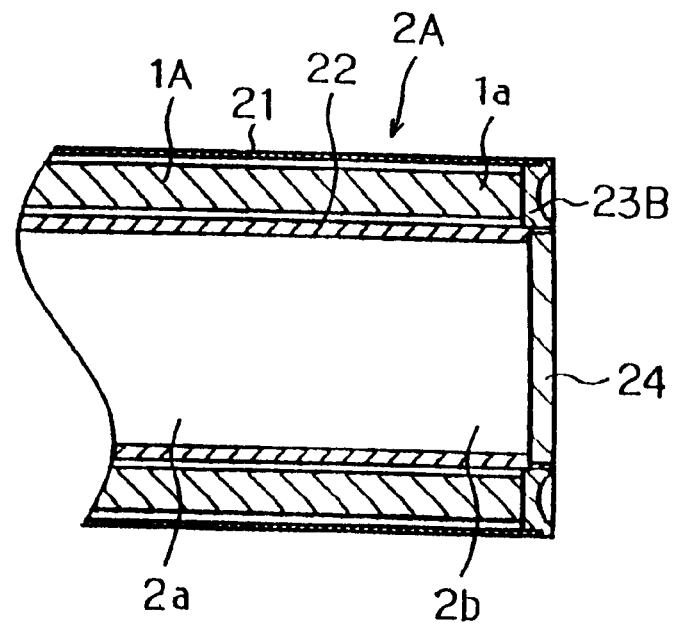
*Fig.2* b

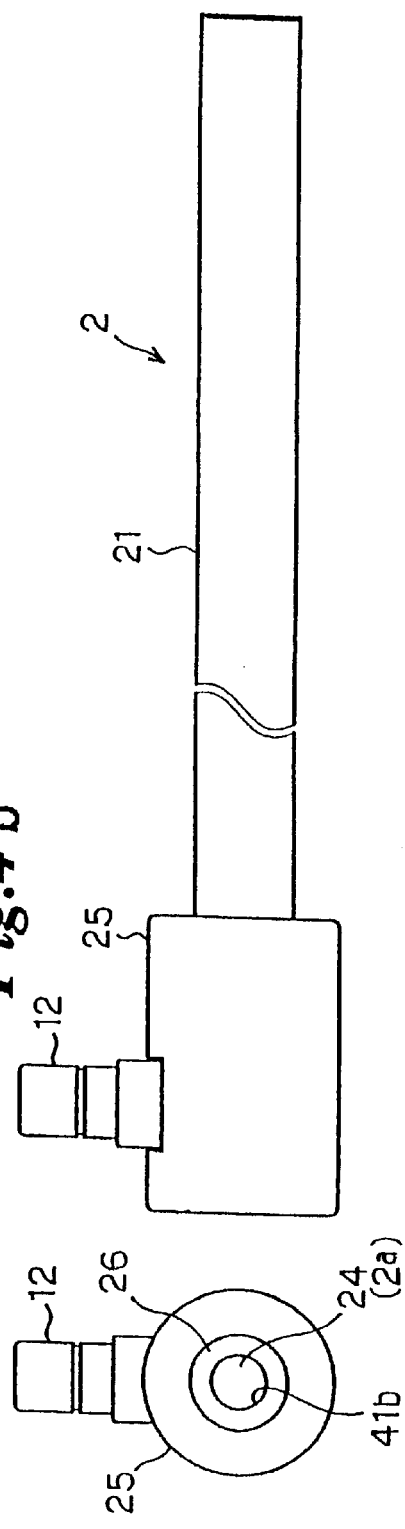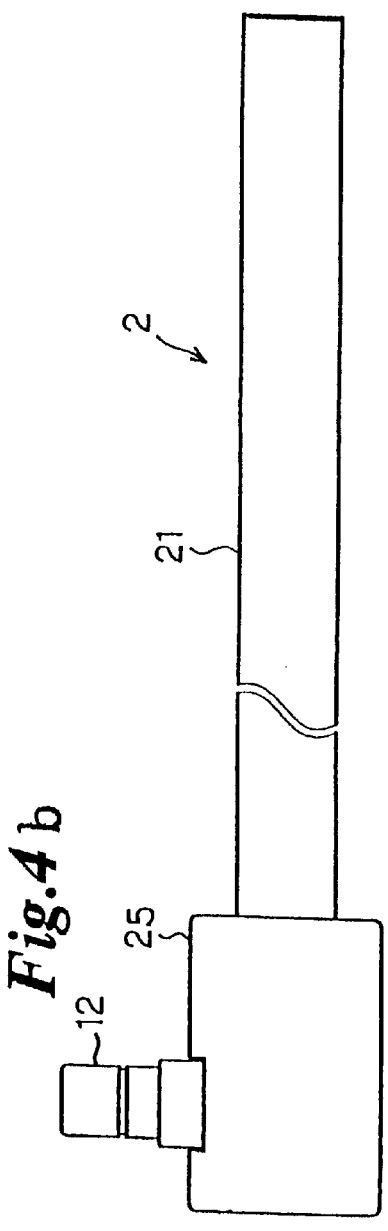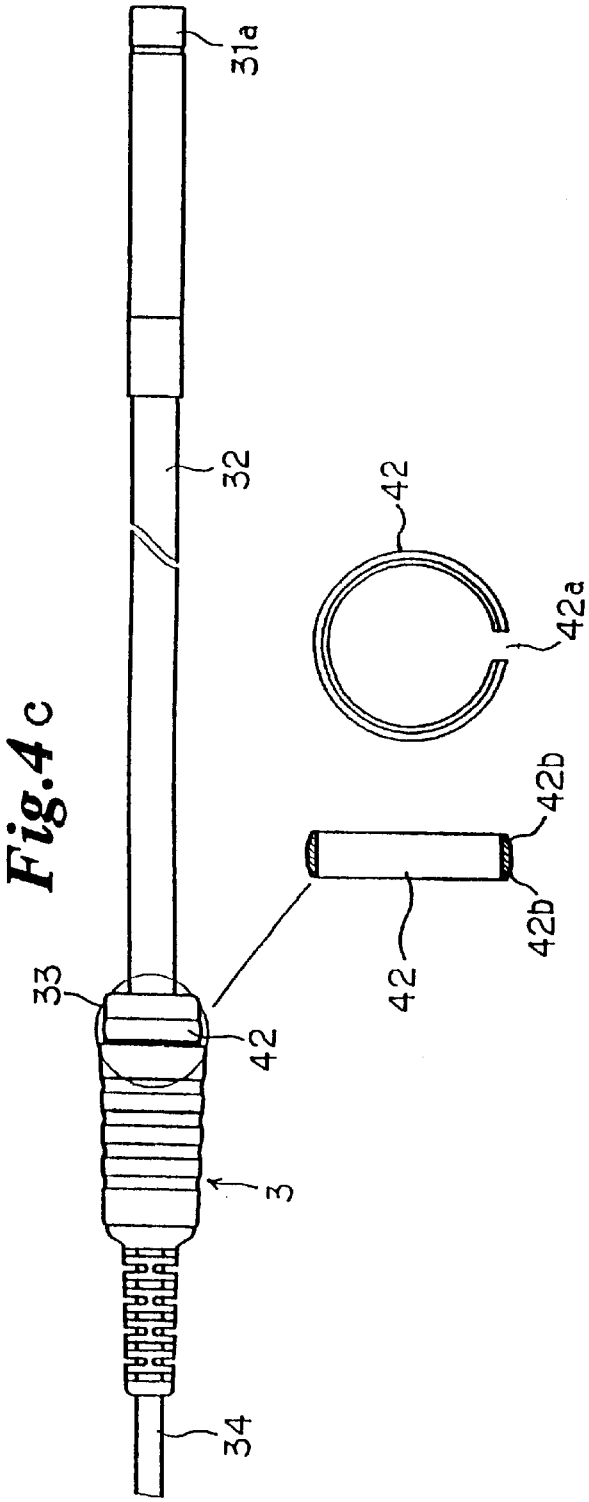

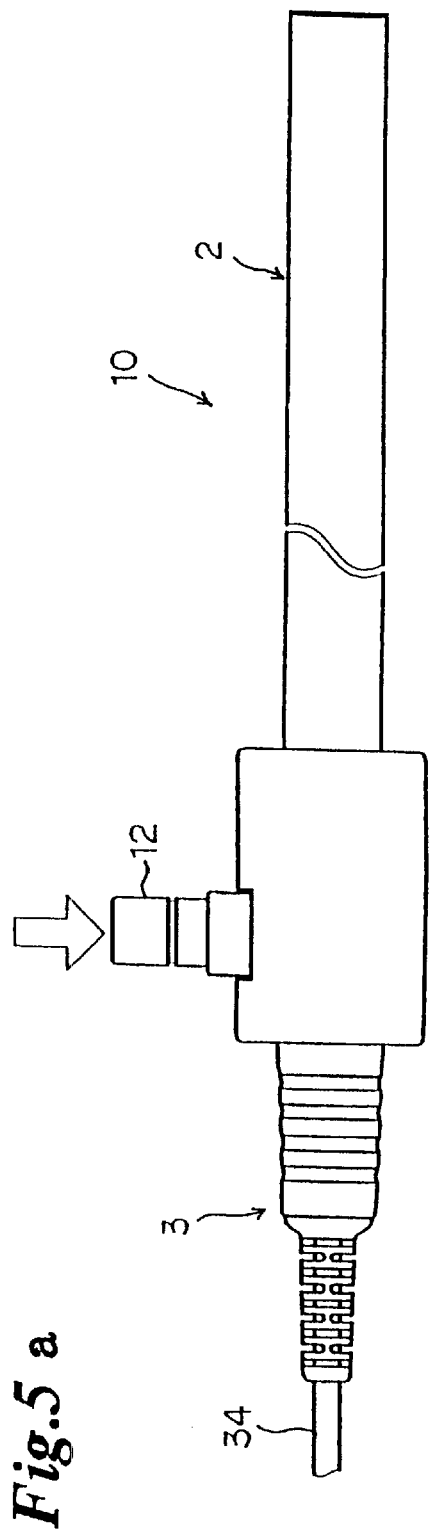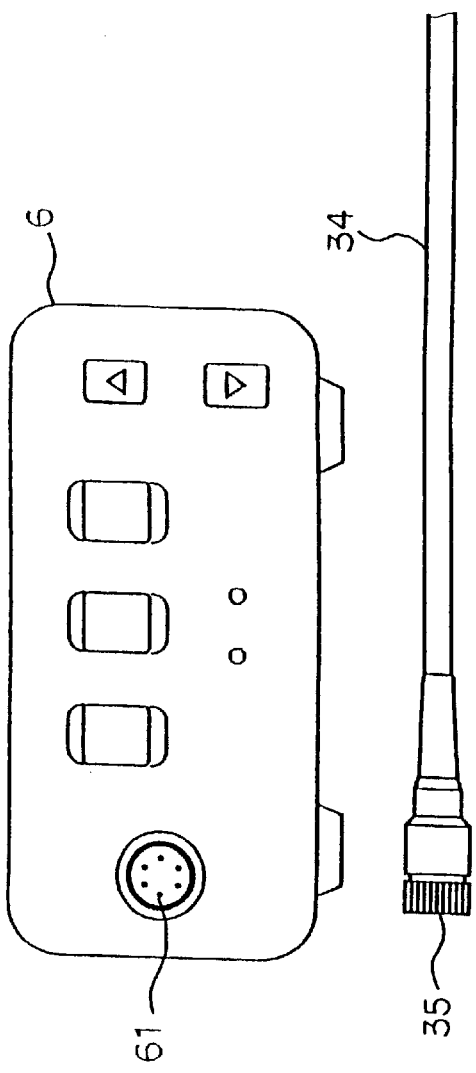
Fig.5 a
Fig.5 b

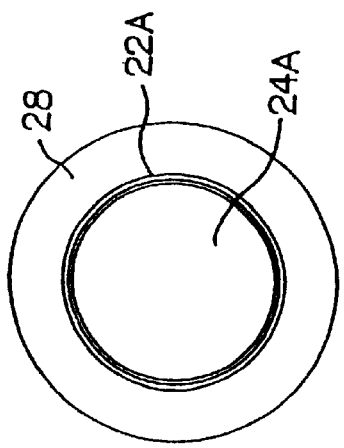
*Fig. 6c*
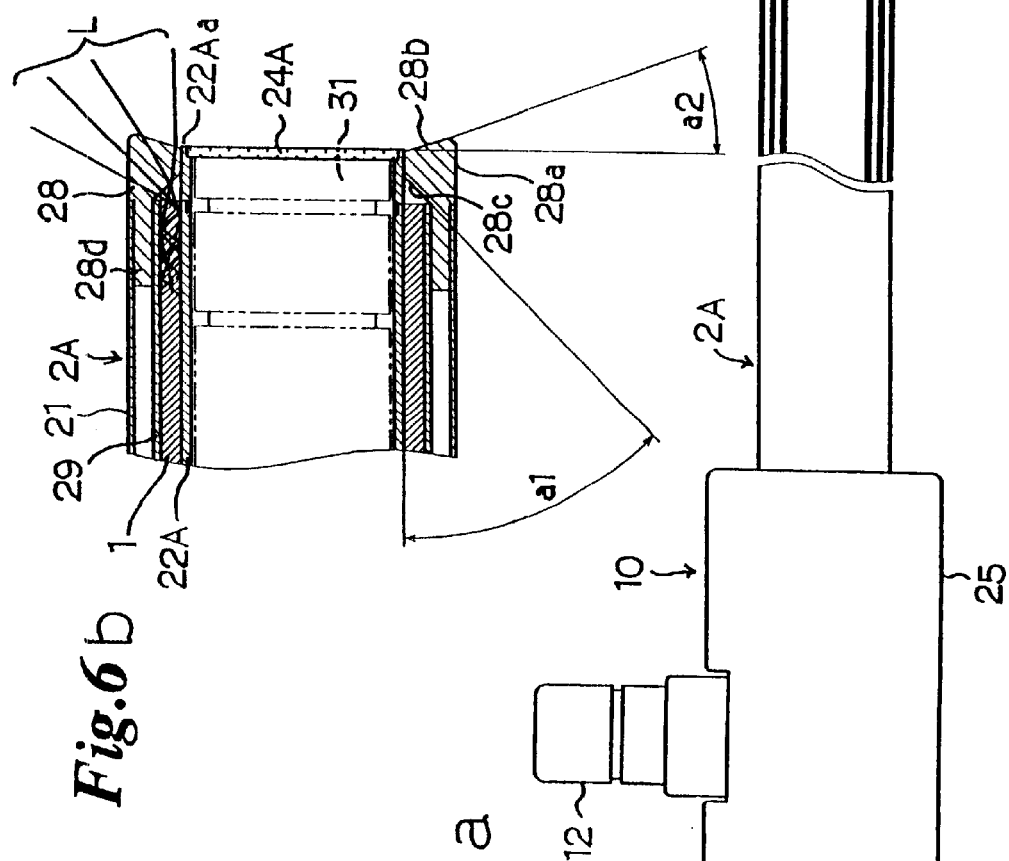
*Fig. 6b*
*Fig. 6a*

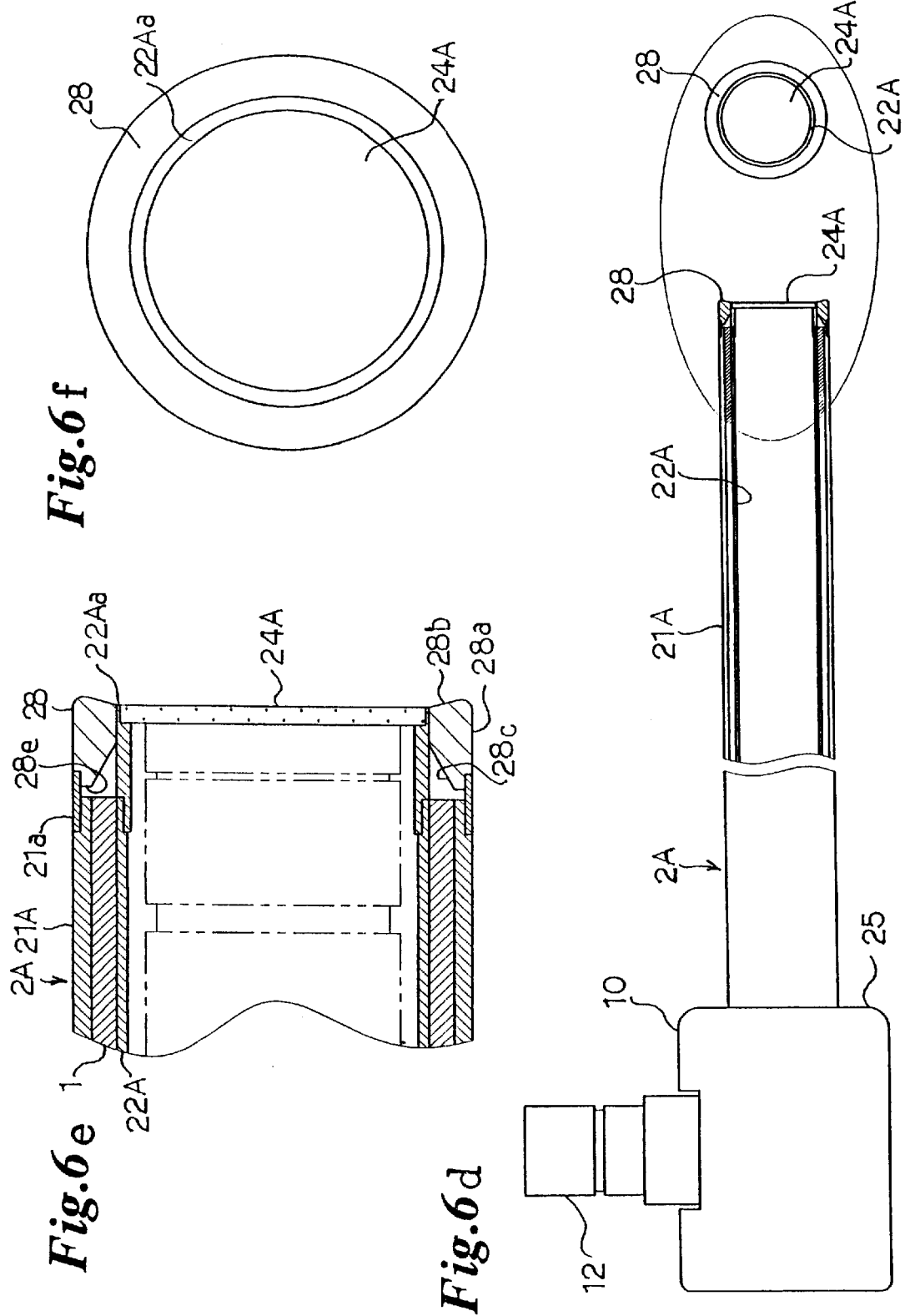

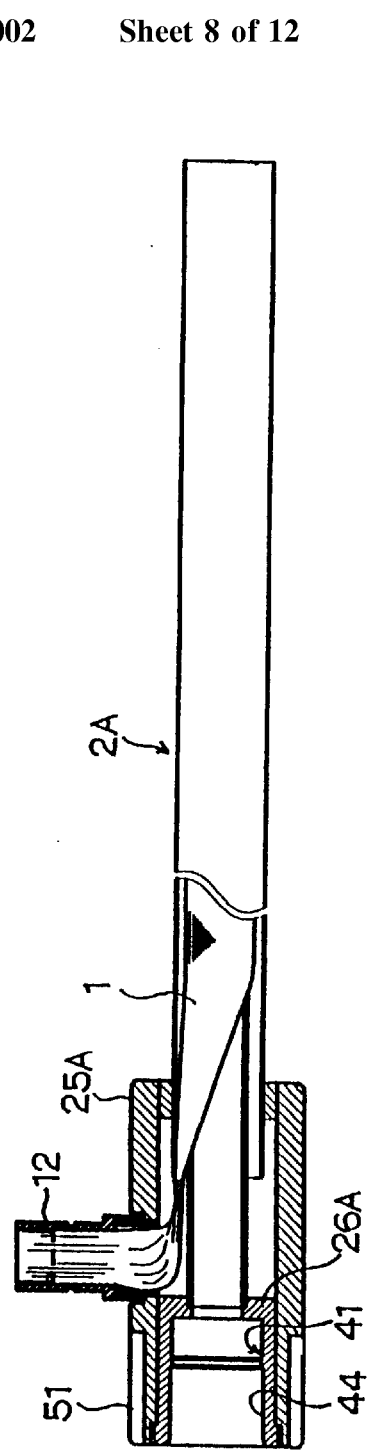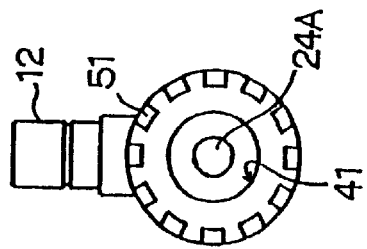

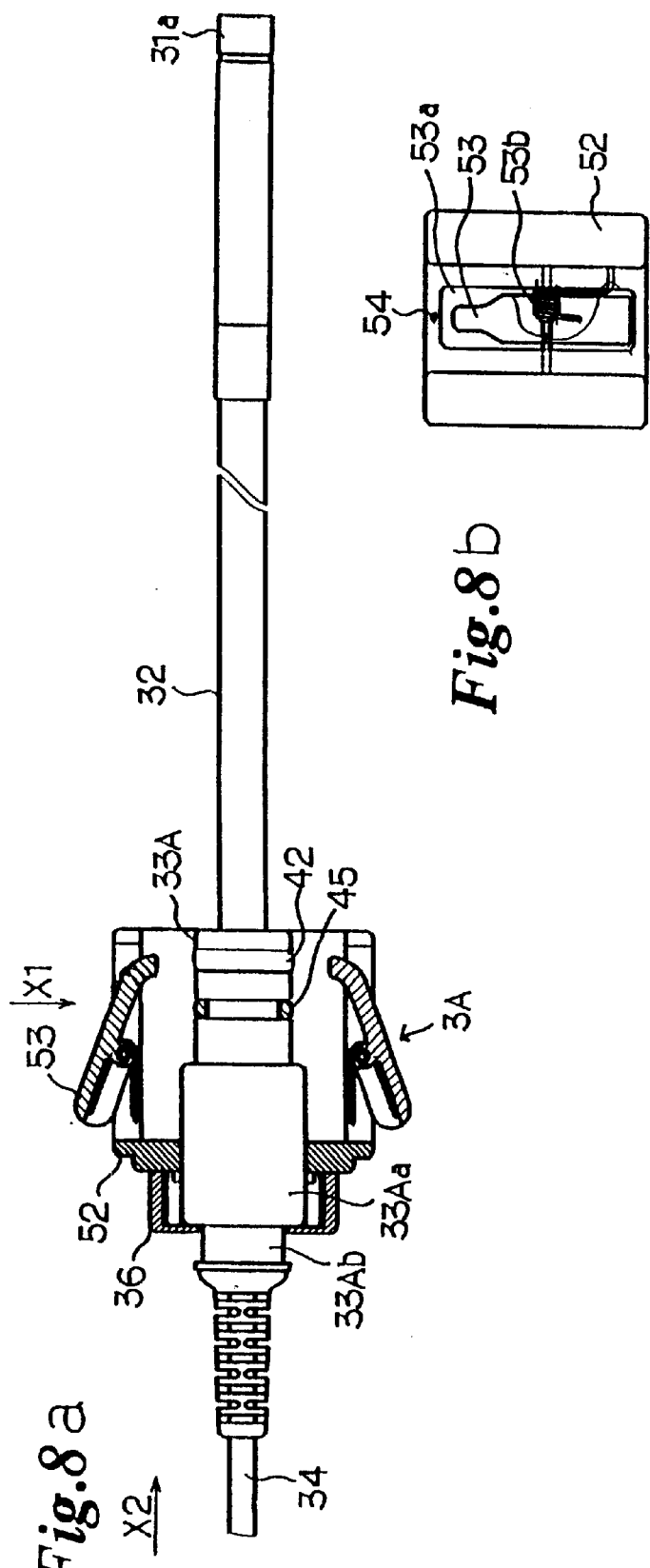
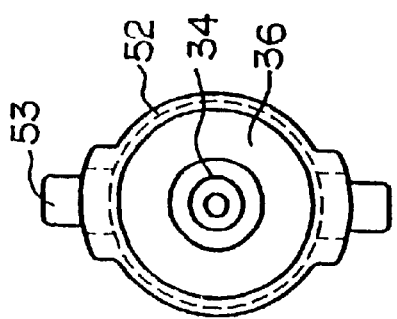
Fig.8a
Fig.8b
Fig.8c

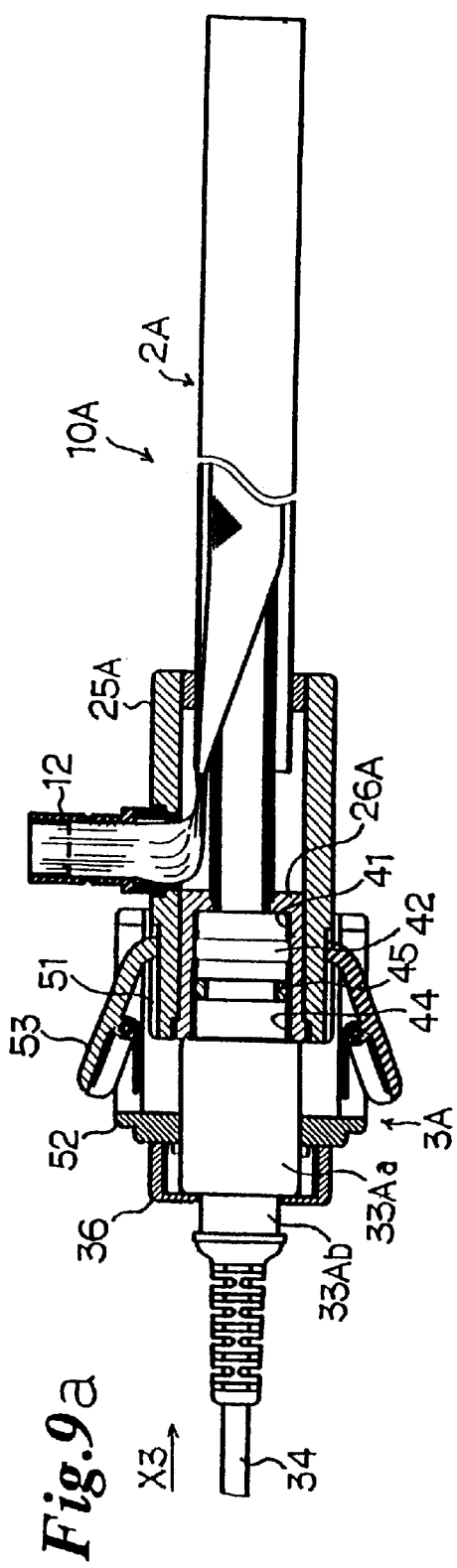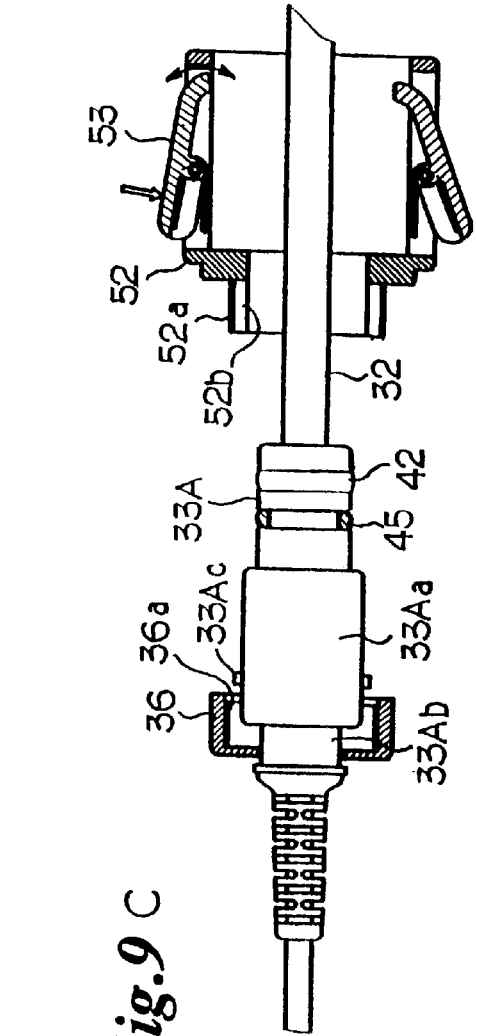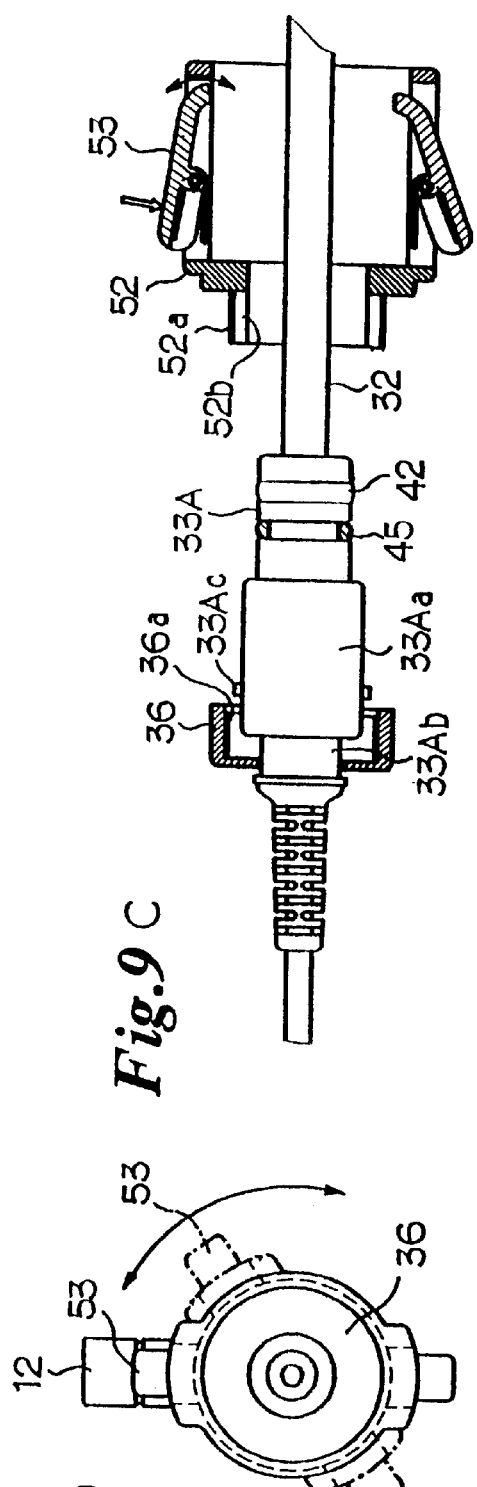

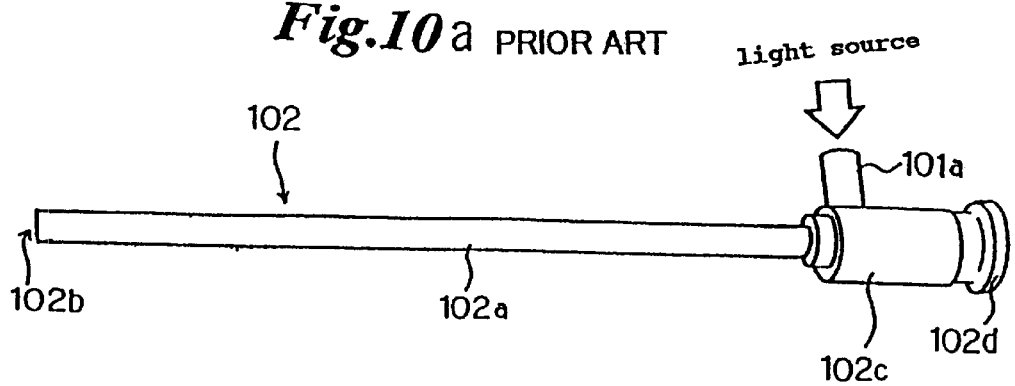
*Fig.10* a PRIOR ART
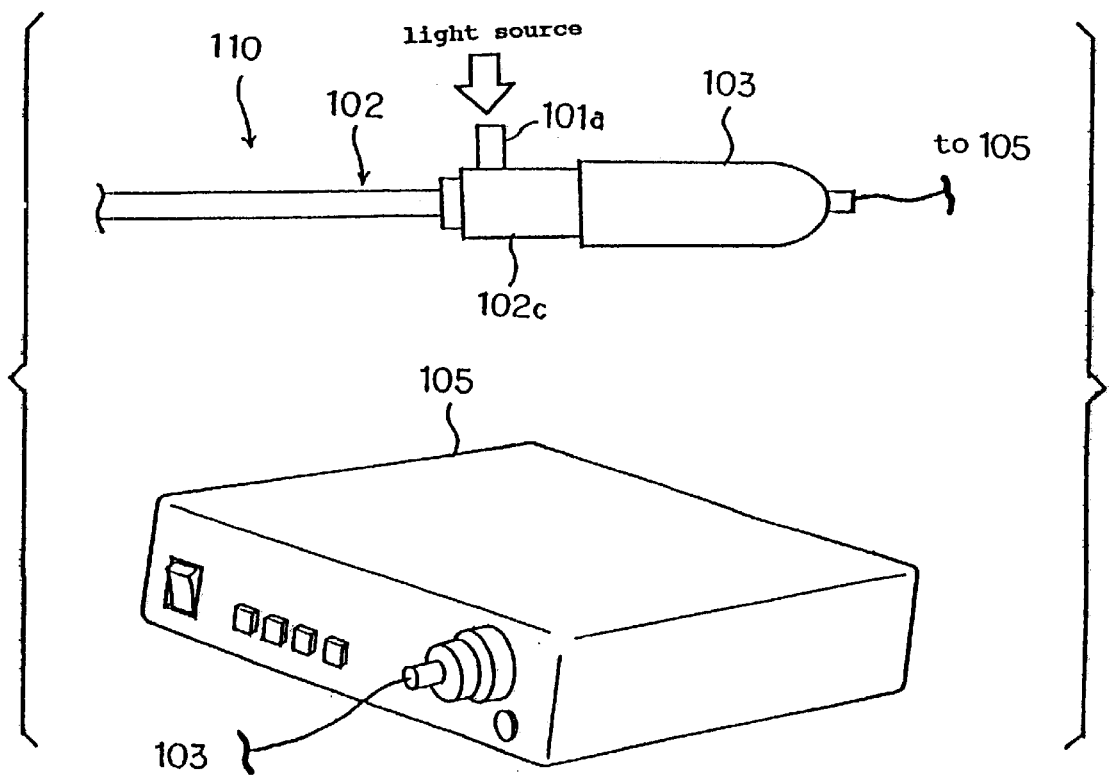
*Fig.10* b PRIOR ART

LAPAROSCOPE APPARATUS

BACKGROUND OF THE INVENTION

1. Field of the Invention

The present invention relates to a newly developed laparoscope apparatus constructed such that a cannula and an endoscope are detachably combined.

2. Description of the Prior Art

Laparoscope apparatuses are usually used as a basic tool for use in a laparoscopic surgery or the like and constructed such that inevitable information for diagnosing and treatment are given for an operator by visualizing the sight in abdominal cavity. Several kinds of apparatuses as improved in their visualization and operability were proposed heretofore.

FIG. 10a and FIG. 10b show external perspective views of a conventional laparoscope and a laparoscope apparatus respectively.

A laparoscope 102 of FIG. 10a comprises a lens and a hollow cannula 102a in which a light guide (not shown) comprised of plural optical fibers get through and constructed such that a light introduced from a light source port 101a is emitted at its tip end 102b of the cannula 102a for illuminating the object to be observed, i.e. an abdominal cavity so as to observe it from an eyeglass part 102d provided at its rear end 102c.

According to such a laparoscope 102, abdominal cavity can be observed more clearly illuminating by the light guide. However, the angle scope is limited to the range from 70° to 80° because the cannula 102a has limitation not only in the length but also in its external diameter, therefore, a wide-angle image suitable for laparascopic surgery would not have been obtained.

A laparoscope apparatus 110 shown in FIG. 10b comprises a CCD (charge coupled device) camera 103 attached to an eyeglass part as shown in FIG. 10a as reference numeral 102d and constructed such that an image signal obtained by the CCD camera 103 is lead to a control box 105 for displaying on a screen such a CRT (cathode ray tube).

According to this apparatus, plural operators can observe the sight in abdominal cavity at the same time, thereby achieving improvement in convenience, however, the problem of the narrowness of angle of scope as above-mentioned still remains and can't be solved in any way.

FIG. 11 is a partially cut-away front view of another embodiment of a conventional laparoscope.

The laparoscope 112 comprises a light source port 112a of a light guide, a tip end 112b, a rear end 112c and a eyeglass part 112d of a cannula 112a as like the laparoscope 102 shown in FIG. 10a and has a characteristic feature that plural rod lenses 112e which are excellent in an optical characteristics as lenses provided in the cannula 112a, therefore indeed the angle of scope has been enlarged to some extent, however, a desirable angle of scope hasn't been obtained yet.

In addition, according to the conventional laparoscope as above-mentioned, a minute image of a subject would not have been also obtained clearly due to the fact that an image-picking means is attached to the cannula on its outside whereas the subject to be observed exists outward the cannula, therefore they locate apart from each other anyhow.

SUMMARY OF THE INVENTION

The present invention has been proposed to solve the above-mentioned problems.

Accordingly, it is an object of the present invention to provide a laparoscope apparatus which can obtain scope of wide angle and clear and minute image of sight in a cavity suitable for laparoscopic surgery or the like and which has also good facilities for operation and maintenance.

According to the present invention, a laparoscope apparatus for use in laparoscopic surgery or the like comprises a cannula with an inner hollow having therein a light guide means for introducing light to its tip end for illuminating an object to be observed. The cannula is sealed with transparent member at its tip end of the inner hollow for preventing of encroaching of water, preferably airtightly sealed. The laparoscope apparatus further comprises an endoscope capable of being pulled into and out from the inner hollow of the cannula, the endoscope having therein an image-picking up means with a wide-angle lens, and the image-picking up means being disposed close to the transparent member in the cannula.

The "cannula" generally means an intubation for feeding liquid or air into an abdominal cavity for use in laparoscopic surgery or the like. However, in this specification, it includes a tubular member provided therein with a light guide for illuminating and used as a cylindrical container into which an endoscope is to be inserted. The endoscope generally includes a fiberscope, however in this specification, such an apparatus with an image-picking up means at its tip end constructed such that the image signal can be taken out of its rear end and both ends are connected to a flexible or a non-flexible cable is also included. "The image-picking up means being disposed close to the transparent member" means include such apparatus that the face of taking image contacts with the transparent member for observing.

It is a characteristic of the present apparatus that the endoscope is constructed such that it is detachable with the cannula. According to such a construction, they are combined with each other only when used and can be handled as separated members when cleaning and sterilizing it after use of them, and therefore, for instance, different sterilization suitable for each of the cannula and endoscope may be selectively applied.

Especially for the cannula, although it is required to be sterilized under strict state because it directly touches organs in abdominal cavity, according to the present apparatus, such a strict sterilization may be applied because the laparoscope housing an image-picking up means such a CCD camera can be easily detached from the cannula.

By the way, although an alcohol cleansing is a well known cleansing method, a general autoclave sterilization, EOG (ethylene oxide gas) sterilization which is effective at about 70° C., and a plasma sterilization which is effective at about 40° C. or 70° C. may also be applied as a concrete sterilization method.

For example, one kind of sterilization may be applied to the endoscope and, while plural kinds of sterilization may be applied to the cannula. Further, it may be possible that alcohol is applied to only the endoscope but strict sterilization is applied to the cannula.

The endoscope to be combined with, or incorporated into the cannula is characterized in that the image-picking up means having a wide-angle lens is disposed close to the tip end of the cannula. According to such construction, a scope with wide angle can be obtained so that more detailed and clear image can be obtained, therefore, the endoscope more suitable for laparoscopic surgery or the like can be provided.

Further according to the laparoscope apparatus of the present invention, the light guide has a light emitting surface formed in such annular shape that it surrounds the transparent member and an annular diffusion cover is further provided at a part of the cannula which touches the light emitting surface for outwardly diffusing illuminating light emitted from the emitting surface of the light guide in the peripheral direction.

According to the apparatus, about the periphery of the tip end of the endoscope, namely an illuminating part to be observed can be uniformly illuminated because the annular diffusion cover is disposed at the tip end of the cannula, therefore illuminating light through the annular diffusion cover spreads widely in an abdominal cavity without locally concentrating in one direction so that halation caused when only specified part is strongly illuminated is effectively prevented and is also prevented from existing such a part where illumination is not applied.

Still further according to another embodiment of the laparoscope apparatus of the present invention, the light guide is constructed such that on its end side of its annular diameter is gradually enlarged in the direction toward the front of the cannula.

According to the embodiment, since the annular shape constituting an illuminating part is constructed such that it is enlarged outwardly around the endoscope housed in the cannula, in other word, the annular diameter is gradually enlarged toward the end of the cannula, halation can be effectively prevented even when the light is annually emitted in parallel.

Moreover, in another embodiment of the present invention, the annular diffusion cover is comprised of an annular concave lens.

According to the embodiment, light emitted from the light guide is reflected by the annular lens or the light guide prism provided at the tip end of the cannula respectively in each embodiment and is outwardly directed in the peripheral direction but is not directed in the front direction. Therefore, light emitted from the light guide is prevented from concentrating on one part and therefore is uniformly and widely diffused by the concave lens or the guide prism so that halation as above-mentioned can be also effectively prevented. Hence, the apparatus may be more suitable for picking up the image of the sight in abdominal cavity at wide-angle.

Still further, according to other embodiment of the present invention, the light guide prism has a light diffusion surface at least one end of either its incident or its emission end.

According to another embodiment of the present invention, the endoscope can be separated from and incorporated into the cannula by pulling it into or pulling out from the cannula by easy manual operation: wherein one embodiment is characterized in that the cannula further comprises an installation means having an association hole into which the endoscope is inserted and the endoscope is attached with a resiliently deformable fitting member, the fitting member being resiliently deformed so as to allow the detachment of the endoscope from the cannula, when the endoscope is pulled into and from the association hole of the installation portion and, whereas in another embodiment simultaneously proposed, the cannula further comprises an installation means having plural association grooves and an association hole into which the endoscope is inserted and the endoscope is attached with a fitting member with an association claw, the fitting member being constructed such that the association claw is engaged with any of the association grooves by inserting the endoscope attached with the fitting member into the association hole with the association claw opened and thereafter closing the association claw.

BRIEF DESCRIPTION OF THE DRAWINGS

FIG. 1a shows a partial vertical section of one embodiment of a laparoscope apparatus of the present invention.

FIG. 1b is a detailed view of the tip of an endoscope.

FIG. 1c is a detailed view of the tip of a cannula.

FIG. 2a and FIG. 2b show partial vertical section of another embodiment of the tip of a cannula.

FIG. 4a is an external rear view of a cannula of one embodiment of the present invention.

FIG. 4b is a front view of the same.

FIG. 4c is an external front view of an endoscope of this embodiment of the present invention.

FIG. 5a shows entire view of the laparoscope apparatus of one embodiment when an endoscope is incorporated into a cannula.

FIG. 5b shows an external view of a rear end of an endoscope and a control box respectively.

FIG. 6a is a front view of a vertical section of a cannula in another embodiment of the present invention.

FIG. 6b is an enlarged vertical section of the embraced part by an ellipse shown in FIG. 6a.

FIG. 6c is front view of the same.

FIG. 6d is a front view of a vertical section of a cannula in still another embodiment of the present invention.

FIG. 6e is an enlarged vertical section of the embraced part by an ellipse shown in FIG. 6d.

FIG. 6f is front view of the same.

FIG. 7a is a rear view of the cannula shown in FIG. 6a.

FIG. 7b is a front view of the cannula shown in FIG. 6a, showing a vertical section of its rear end.

FIG. 8a shows a front view of an endoscope of the present invention with an installation means of an alternate embodiment.

FIG. 8b is a fragmental view shown from the direction of the arrow X1.

FIG. 8c is a fragmental view shown from the direction of the arrow X2.

FIG. 9a shows a laparoscope apparatus when the endoscope of FIG. 7 is inserted into the cannula of FIG. 6.

FIG. 9b is a fragmental view taken in the direction of the arrow X3.

FIG. 9c is a view explaining the endoscope can be disassembled.

FIG. 10a is an external perspective view of the conventional laparoscope.

FIG. 10b is an external perspective view of the conventional laparoscope apparatus.

DETAILED DESCRIPTION OF THE INVENTION

Figure 3B:
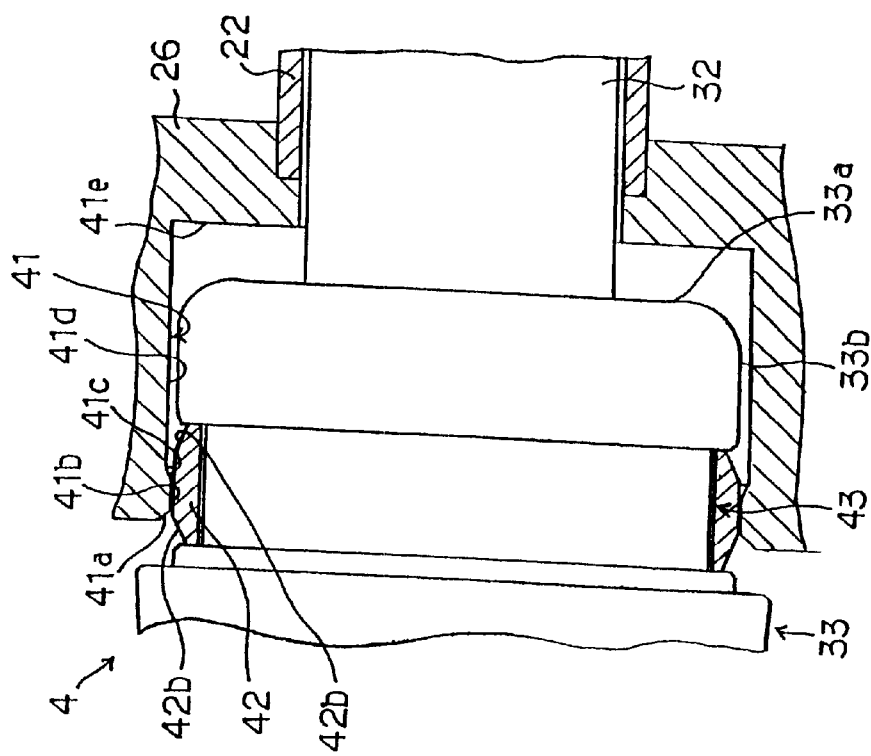
FIG. 3b shows a partial section of the installation means having an association hole into which an endoscope attached with a fitting member is not completely engaged.

Now, preferable embodiments of a laparoscope apparatus according to the present invention will be explained referring to the attached drawings.

FIG. 1a is a partial vertical section of one embodiment of a laparoscope apparatus of the present invention, FIG. 1b is a detailed fragmentary cross sectional view of the tip end of an cannula, and FIG. 1c is a external view of the tip of a cannula.

A laparoscope apparatus 10 comprises a cannula 2 provided with a light guide 1 for leading light to its tip end for illuminating an object to be observed and an endoscope 3 incorporated into an inner hollow 2a of the cannula 2 from its rear end in a manner described later.

A light guide 1 is composed of plural optical glass fibers in the form of bundle where light is transmitted without attenuating, or almost without any loss of light energy.

The light emitting surfaces 1a of the plural fibers are annularly arranged at tip end of cannula 2 in a manner they surround the transparent member 24 disposed in the center of the cannula 2 and an annular diffusion cover 23 is attached to the end tip of the inner hollow of the cannula 2 so as to diffuse light emitted from plural glass fibers outwardly in peripheral direction.

The light guide 1 comprised of plural optical fiber leads the light fed from its end to another end without attenuating and can properly refract the light according to its setting position or the sectional shape of the bundle and it can be formed in such shape as circular or ring-like for its purpose.

The cannula 2 is of a dual layer type comprised of an outer cylinder 21 and an inner cylinder 22. The light guide 1 is provided between the outer cylinder 21 and the inner cylinder 22 and its tip end 1a, i.e. a light emitting surface is formed in an annular shape conforming to the shape of a clearance between the cylinders 21 and 22. A tip guide 11 and the light emitting surface 1a of light guide 1 is disposed in the clearance between the cylinders 21 and 22 for keeping an annular shape. The tip end 2b of the inner hollow 2a in the inner cylinder 22 is sealed with a transparent member 24, whereas the light emitting surface 1a is sealed with an annular transparent cover 23, therefore there is no fear of contamination when the cannula 2 is inserted into abdominal cavity. Further because the tip end 2b of the hollow 2a of the cannula 2 where the endoscope 3 is inserted is sealed with the transparent member 24, the endoscope 3 isn't polluted in abdominal cavity and an image-picking up means 31 disposed in the cannula 2 is not hidden.

The light emitting surface 1a may be made as a separate member from the transparent member 24, or they may be integrated in such a manner that both of them may be made of one piece of clear glass plate. In this case, sealing of the connecting part between the transparent cover 23 and the transparent member 24 can be omitted and can be sealed more certainly. And in this case, only the one side corresponding to the light emitting surface 1a is treated to form a frosted glass surface in order to diffuse illuminating light at random, random diffusion effect by the light emitting surface 1a can be obtained, and the effect will be explained hereinafter.

In the above-mentioned embodiment, the light emitting surface 1a of the light guide 1 is sealed with the transparent cover 23, however, when the light emitting surface 1a composed of optical fibers is processed to form a light diffusing surface by executing a frosting process and the emitting surface 1a of the light guide 1 is so constructed to keep the same surface as the tip end of the cannula 2 without any clearance, it may be not necessary to provide the transparent cover 23 as a separate member for sealing. In that case, the tip end 1a of the light guide 1 may be directly exposed at the tip end of the cannula 2 and it can be effectively sealed for preventing encroaching of water.

A rear end cylinder 25 constituting a installation means, which will be described later, is provided at the rear end of the outer cylinder 21 and the inner cylinder 22. And the rear end cylinder 25 has a supporting portion 27 for the outer cylinder 21 and a connection portion 26 for supporting the inner cylinder 22. The connection portion 26 comprises an association means 4 for incorporating the endoscope 3 by simple manual operation. The association means 4 will be described hereinafter.

The rear end cylinder 25 is further provided with a light source port 12 electing against the longitudinal direction of the cannula 2 and from which the light guide 1 is introduced. In such construction, when light is supplied from a light source (not shown), the light is emitted from the light emitting surface 1a of the light guide 1 and transmits through the transparent cover 23 to forwardly illuminate around the tip end of the cannula 2a.

The endoscope 3 is provided near to its tip end 2b with an image-picking up means 31 which comprises a wide-angle lens 31a and a CCD camera (charge coupled device) 31b and the image-picking up means 31 is disposed close to the transparent member 24 in the cannula 2.

By the way, the word of "close to" in this description includes the meaning of the case in which the wide-angle lens 31a of the image-picking up means 31 is disposed in a manner it contact with the transparent member 24.

The endoscope 3 comprises the image-picking up means 31 such as a CCD camera, a connection cylinder 32 in which the image-picking up means 31 detachably housed at its tip end, a base body 33 which is a base of the connection cylinder 32 and constitutes the association means 4, and a connecting cable 34 extending from the base body 33. The connecting cable 34 is connected to the control box 6, which will be explained hereinafter.

According to such a laparoscope apparatus 10, the endoscope 3 can be detachably incorporated into the cannula 2. Therefore, they are integrated when used for an laparoscope apparatus 10 as mentioned above, and they can be treated separately for appropriate sterilization respectively after used.

The cannula 2 is required to be sterilized under strict state because it directly touches the organ in abdominal cavity. Such a strict sterilization can be executed because the endoscope 3 housing the image-picking up means 31 can be separated from the cannula 2.

On the other hand, antisepsis such as low temperature disinfection may be executed for the endoscope 3 because it is used in the cannula 2 and isn't directly exposed in abdominal cavity.

The endoscope 3 is constructed such that the image-picking up means 31 comprised of the wide-angle lens 31a and the CCD camera 31b come close to or contact with the transparent member 24 at the tip end in the cannula 2. Therefore, wide angle of scope can be obtained due to close positioning of the image-picking up means 31 to the subject to be observed so that more clear and detailed image of sight in the abdominal cavity can be obtained.

Accordingly its operability is improved and becomes suitable for laparoscopic surgery or the like.

For example, operation mistakes of a forceps and an electric cautery used for laparoscopic surgery can be reduced so that safety of laparoscopic surgery can be enhanced. Further since the operability of a forceps and an electric cautery is improved, operation time is reduced, operations of a laparoscope apparatus is familiarized in a short time, thereby helping popularization of laparoscopic surgery. Furthermore, plural lenses housed in the cannula as used in the prior art aren't required, so its product cost can be also lowered. The light emitting surface 1a of the light guide 1 is formed like a ring shape, or an annular shape so that the light can widely illuminate around the image-picking up means 31 of the endoscope 3, thereby facilitating image-picking up.

If the transparent cover 23 is constructed so as to diffuse light at random by executing a forested glass process, the light from the light emitting surface 1a of the light guide 1 is diffused at random by the light transparent cover 23 so as not to locally concentrate on one spot. Therefore, halation which is caused when only some part is illuminated can be prevented and there exist no place where light isn't illuminated, thereby picturing and observing preferably.

Such a random light diffusion effect can be achieved when the light transparent cover 23 and the light transparent member 24 are integrated or when the light transparent cover 23 is composed of the light emitting surface 1a it self.

Since the light emitting surface 1a of the light guide 1 is formed in an annular shape, or ring-like shape so as to outwardly enlarge the light emitted at emitting surface around the endoscope 3 housed in the cannula 2 in such a manner that the annular diameter of the light guide is enlarged.

Therefore, when ring-like light is illuminated in parallel, halation as above-mentioned can be prevented.

However, when a light emitting surface having a suitable random diffusion effect as shown in FIG. 2 is used, the annular diameter of the light guide 1 isn't always required to be enlarged.

FIG. 2a and FIG. 2b show another embodiment of a tip of cannula including a light guide. The same reference numbers are used for the same members as FIG. 1 and therefore their explanations are omitted hereinafter.

The ring diameter of a light guide 1A of FIG. 2a is uniform and a light transparent cover is constructed as an annular diffusion cover 23A so as to adequately diffuse light at random. According to such construction, halation caused when illuminating light is concentrated around the center can be prevented and the places where illuminating light doesn't reach also can be reduced.

In such construction that only a contacting side of the diffusion cover 23A with the light emitting surface 1a of the light guide 1, namely a light entering side, is preferably formed as a light diffusing surface for diffusing light at random, and while a light emitting side is made smooth, illuminating light emitted via the cover 23A is randomly diffused, in addition, since the light emitting side is made smooth, it may be also preferable from the standpoints of sanitary.

In FIG. 2b, the light guide 1A is employed as the same one as shown in FIG. 2a, however, the light transparent cover is formed as an annular concave lens 23B, so that light emitted from the light guide 1A is effectively diffused. Therefore, halation is not caused and places where illuminating light doesn't reach are reduced.

By the way, as a method of preventing concentration of illuminating light other than above-mentioned method, such method that illuminating light from each optical fiber composed of the light guide 1 is directed in different direction respectively to diffuse illuminating light emitted from each optical fiber by varying the inclination of the light emitting end of each optical fiber may be applied.

According to the one embodiment of the present invention, the cannula further comprises an installation means having an engaging hole into which the endoscope is to be inserted and wherein the endoscope is attached with a resiliently deformable fitting member. The fitting member is resiliently deformed so as to allow the detachment of the endoscope from the cannula when the endoscope is pulled into and from the engaging hole of the installation portion. Such an embodiment will be explained using FIG. 3 and FIG. 4.

Figure 3A:
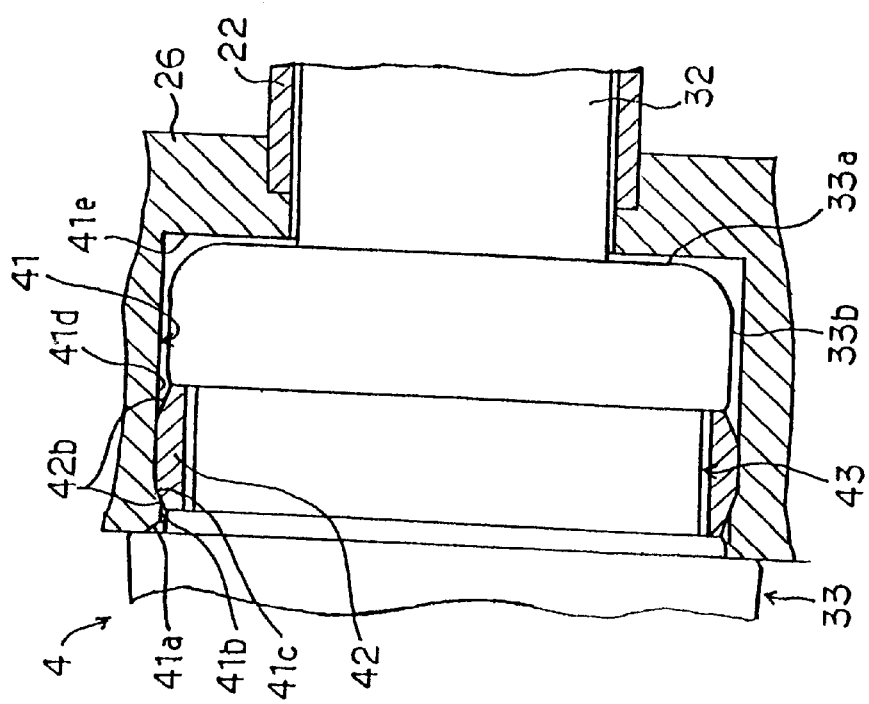
FIG. 3a shows a partial section of one embodiment of the installation means having an association hole into which an endoscope attached with a fitting member is completely engaged.
Figure 11:
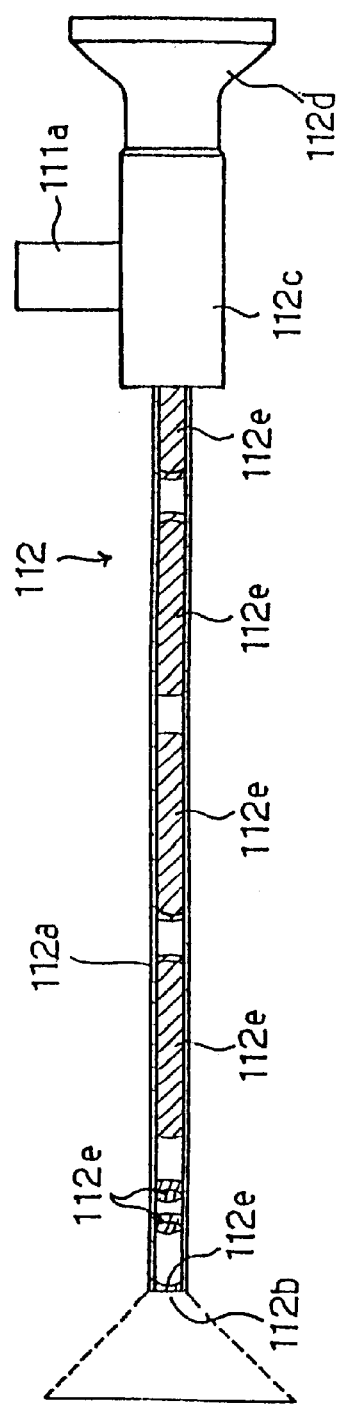
FIG. 11 is a partially cut-away front view showing another embodiment of the conventional laparoscope.

FIG. 3a is a partial section of such embodiment of the installation means having an association hole into which an endoscope attached with a fitting member is completely engaged and FIG. 3b is a partial section of the installation means having an association hole into which an endoscope attached with a fitting member is not completely engaged.

The association means 4 comprises an association hole 41, engaging hole of the installation means, provided at the connection 26 of the cannula 2, a C-ring 42 for associating through easy manual operation as a resiliently deformable fitting member, and an association groove 43 formed in the base body 33 of the endoscope 3.

The association hole 41 is constructed with an inlet inclination 41a at a side of the connection 26 for inserting the endoscope 3, a following inlet small diameter part 41b, a following inner inclination 41c, a following association hole part 41d, and an association bottom 41e forming an undersurface of the association hole part 41d. A hole having the same inner diameter as the inner cylinder 22 supported by the connection 26 is formed at the center of the association bottom 41e so as to insert the endoscope 3.

The C-ring 42, shown in FIG. 4c, which is made of an elastic material and is commercially available, is provided with a cut 42a at a part of its circumference, and also provided with an inclination 42b at both edges of its external diameter. When an advancing force so as to close the cut 42a is applied on the C-ring 42, namely under restrained state, it is elastically deformed so as to make the diameter small comparing to its free state. When the force is released, the C-ring 42 restores its original free diameter because of its elastic restoring force.

The width of the association groove 43 is determined in such a manner that the C-ring 42 can be inserted with small clearance.

The relation among the inner diameter of the C-ring 42, the outer diameter of the C-ring 42, the inner diameter of the inlet small diameter 41b of the association hole 41, the association hole part 41d of the association hole 41, and the outer groove diameter of the association groove 43 is important. There should be following relations among them.

1) outer diameter of restrained C-ring 42< inner diameter of the inlet small diameter 41b of the association hole 41< inner diameter of the association hole part 41d of the association hole 41 $\leq$ outer diameter of free C-ring 42

1) outer groove diameter of the association groove 43 < inner diameter of restrained C-ring 42.

As an additional condition, the outer diameter of a shoulder 33b of the base body 33 of the endoscope 3 is smaller than the inner diameter of the opened C-ring 42 so as to insert the C-ring 42 in the association groove 43 and the outer diameter of the shoulder 33b is smaller than the outer diameter of free C-ring 42 after the C-ring 42 is inserted in the association groove 43.

According to such an association means 4, the endoscope 3 can be inserted into and detached from the cannula 2 by easy manual operation.

At first the C-ring 42 is opened and inserted in the association groove 43 from the shoulder 33b of the base body 33 of the endoscope 3. In this time the C-ring 42 is associated so as not to be dropped out of the association groove 43 and such that the inner diameter of the C-ring 42 is associated with the outer diameter of the association groove 43 while keeping a fixed clearance.

Under such a state, when the endoscope 3 inserted with the C-ring 42 is inserted into the cannula 2, the inclination 42b of the outer diameter of the C-ring 42 is associated with the inlet inclination 41a of the association hole 41. Then the C-ring 42 is elastically deformed and compressed by the inlet inclination 41a and becomes a state in FIG. 3b when the endoscope 3 is inserted.

The inner diameter of the C-ring 42 restricted by the inlet small diameter part 41b of the association hole 41 is larger than the outer diameter of the association groove 43 because of the above-mentioned relations 1) and 2) and the endoscope 3 is further inserted keeping the C-ring 42 deformed so as to be the state in FIG. 3a. The C-ring 42 is expanded so that the outer diameter of the C-ring 42 becomes the same as the inner diameter of the association hole part 41d because of the elastic restoring force of the C-ring 42 under such a state. However, the C-ring 42 still has its elastic restoring force to be restored to its free state because of the above-mentioned relation 1).

According to the relation between the depth of the association hole 41 of the association hole part 41d to the association bottom 41e and the width of the shoulder 33b of the base body 33 and the association groove 43, the other side of the outer diameter inclination 42b of the C-ring 42 is associated with the inner inclination 41c of the association hole 41 while a front 33a of the shoulder 33b comes close to the association bottom 41e, the endoscope 3 is enforced by the remained elastic restoring force in such a manner that the front 33a of the base body 33 keeps close to the association bottom 41e, and the image picking-up means 31 of the endoscope 3 is positioned so as to come close to the transparent member 24 of the cannula 2.

Accordingly, the endoscope 3 can be easily associated at a given position only by an easy manual operation that the endoscope 3 is inserted in the association hole 41 of the cannula 2.

When pulling force is applied so as to extract the endoscope 3 under the state of FIG. 3a wherein the outer inclination 42b of the C-ring 42 is associated with the inner inclination 41c of the association hole 41, the C-ring 42 is elastically deformed and shrunk regulated by the inner inclination 41c and the inlet small diameter 41b of the association hole 41 because of the pulling force, as shown in FIG. 3b. The endoscope 3 can be easily extracted keeping the C-ring 42 elastically deformed like when it is inserted, therefore extraction through one-touch operation can be achieved.

FIG. 4a is an external rear view of a cannula of one embodiment, FIG. 4b is its front view, and FIG. 4c is an external front view of an endoscope of the embodiment.

As shown in FIGS. 4a and b, the hollow 2a of the cannula 2 penetrates from the inlet small diameter part 41b of the association hole 4 provided at the connection 26 and the transparent member 24 of the tip 2b of the cannula 2 is seen from the rear.

The C-ring 42 is inserted in the association groove 43 of the base body 33 of the endoscope 3 at free state as shown in FIG. 4c.

FIG. 5a shows an entire view of a laparoscope apparatus of one embodiment when an endoscope is incorporated into a cannula, and FIG. 5b shows an external view of a rear end of the endoscope and a control box.

FIG. 5a shows when the endoscope 3 is set in the cannula 2 and FIG. 5b shows that a connecting terminal 35 is provided for the connecting cable 34 of the endoscope 3 and a connecting terminal 61 corresponding to the connecting terminal 35 is provided for the control box 6.

When the connecting terminals 35 and 61 are connected so as to connect a line to the light source, the image picking-up means 31 of the endoscope 3 of the laparoscope apparatus 10 and lighting of the light guide 1 can be controlled by the control box 6.

Next another embodiment of laparoscope apparatus of the present invention will be explained hereinafter.

FIG. 6a is a front view of a vertical section of a cannula of another embodiment of the present invention, FIG. 6b is an enlarged vertical section of the embraced part by an ellipse in FIG. 6a, and FIG. 6c is its anterior view. The same reference numbers are used for the same members as the already explained embodiment and their explanations are omitted hereinafter.

The cannula 2A is provided with an annular light guide prism 28 at its tip end to which light illuminated from the light guide 1 is entered and from which the light is emitted as a refracted light L which is refracted to the forward periphery of the cannula 2A.

The prism 28 is made of an optical glass or a clear synthetic resin which refracts light at uniform refraction factor and is an annular shape with triangular section. One surface of the triangular section comprises a peripheral light emitting end surface 28a for refracting the entered light having the same outer diameter as that of the cannula 2A and for emitting in peripheral direction, other surface comprises a light emitting end surface 28b for refracting the entered light and for emitting in peripheral direction from the end of the cannula 2A, and an other surface comprises a light entering end surface 28c for receiving the light emitted from the light guide 1. The prism is provided with an inserting part 28d to be inserted into the end of the cannula 2A.

The light entering end surface 28c of the prism 28 is inclined at a given incident surface angle a1 against a light axis of the light guide 1 and the light emitting end surface 28b is inclined at a given emitting surface angle a2 against the end of the cannula 2A. The incident surface angle a1 and the emitting surface angle a2 are determined by trial and error based on an optical theory. According to the research of the present inventors, it is preferable that a1=30°~45° and a2=10°~30° when the light entered from the light guide 1 is emitted as the refracted light L which is widely refracted into the forward periphery of the cannula 2A. The light entering end surface 28c is roughly treated like a frosted glass for introducing the light into the prism by diffusing the light at random. Such a rough surface treatment may be provided for the light emitting end surfaces 28a or 28b. Or any two of them may be roughly treated or all of them may be roughly treated. Such a rough treatment for randomly diffusing light has an effect so as to diffuse the emitted light uniformly while keeping the entire refraction tendency of the refracted light L refracted into the forward periphery of the cannula 2A.

The cannula 2A is different from the cannula 2 in FIG. 2 in that the prism 28 is provided. Further it is different in the followings.

The light guide 1 of the cannula 2A is positioned between an inner cylinder 22A and a light guide cylinder 29 further provided in the outer cylinder 21 of the cannula 2A. It is because that the outer diameter of the tip of the light guide 1 is given shape so as to be inserted with the inserting part 28d of the prism 28.

The inner cylinder 22A reaches the tip of the cannula 2A comparing to the inner cylinder 22 of the cannula 2. A tip 22Aa thereof works as a light shielding wall against the inner diameter side of the prism 28 and a step is provided in the inner diameter side and the transparent member 24A is tightly provided for the step. However, it is possible to integrate the prism 28 and the transparent member 24A without providing the tip 22Aa. In such a case, the incident light in the prism 28 is reflected from a part corresponding to the transparent member 24A and a clear image can't be obtained. Therefore, the prism 28 and the transparent member 24A are separated by the tip 22Aa so as to shield a light.

According to such a cannula 2A, the emitted light doesn't concentrate at a forward center of the cannula 2A so that halation can be prevented. Further, light is dispersed intiperipheral direction so as to be uniformly illuminated at wide angle, therefore it is suitable for a wide-angle picturing.

FIGS. 6d, 6e, 6f shows a partially modified embodiment of the cannula shown in FIGS. 6a, 6b, 6c.

The cannula 2A doesn't have the light guide cylinder 29 for giving shape of the outer diameter of the light guide 1 and its function is accomplished by an outer cylinder 21A unlike the cannula in FIGS. 6a, 6b, 6c. The outer cylinder 21A also insert and support the outer diameter of the prism 28. Therefore, the outer cylinder 21A is provided with an auxiliary ring 21a for connecting the outer diameter of the prism 28 and the outer diameter of the outer cylinder 21A. The shape of an inserting portion 28e of the prism 28 is formed so as to corresponds to the outer cylinder 21A and the auxiliary ring 21a.

In such a manner, one part, the light guide cylinder 29, becomes unnecessary and also the space between the light guide cylinder 29 and the outer cylinder 21 becomes unnecessary. Therefore, the cylinder part of the cannula 2A, namely the outer diameter of the outer cylinder 21A, can be made small and on the other hand, the inner diameter of the inner cylinder 22A can be made large as the reduced size, thereby an endoscope with larger outer diameter can be inserted.

According to another embodiment, the cannula further comprises an installation means having plural association grooves and an engaging hole into which the endoscope is to be inserted and wherein the endoscope is attached with a fitting member with association claw. The fitting member is constructed such that said association claw is engaged with any of the association grooves by inserting the endoscope attached with the fitting member into the engaging hole with the association claw opened and thereafter by closing said association said claw. Such an embodiment will be explained hereinafter referring to FIGS. 7–9.

FIG. 7a is a rear view of the cannula of FIG. 6 and FIG. 7b is a front view of a vertical section of the rear end of the cannula.

The rear end is different from that of the cannula 2 in FIG. 1 in that a rotary association means 5 is provided for a rear end cylinder 25A in addition to the association means 4.

Therefore, the association groove 51 is provided at a rear end periphery of the rear end cylinder 25A so as to equally divide the periphery. Further, a connection 26A inserted in the rear end side of the rear end cylinder 25A is provided with an auxiliary association hole 44 in addition to the association hole 41 comprising the association means 4.

FIG. 8a to FIG. 8c show an alternate embodiment of an installation means: wherein FIG. 8a is a front view of a vertical section of the rear end of an endoscope to be inserted in the cannula, FIG. 8b is a fragmental view taken in the direction of the arrow X1, and FIG. 8c is a fragmental view taken in the direction of the arrow X2.

The shape of a base body 33A of the endoscope 3A is different from that of the endoscope 3 in FIG. 1 and further a rotary cylinder 52 with plural association claws 53 are associatably provided so as to be rotated with the endoscope via a cap nut 36.

The C-ring 42 comprising the association means 4 is inserted forward the base body 33A like the base body 33 of the endoscope 3 and an O-ring 45 is inserted at its rear so as to keep airtight between the cannula 2A and the endoscope 3A. A guide cylinder part 33Aa is further provided and a groove for the cap nut 33Ab is also formed. Then the inner diameter of the side end of the rotary cylinder 52 is inserted into the guide cylinder part 33Aa and the cap nut 36 is rotatably and outwardly inserted into the groove 33Ab. The association of the cap nut 36, the rotary cylinder 52, and the guide cylinder part 33Aa will be explained hereinafter.

When the endoscope 3A is inserted in the cannula 2A, the part provided with the rotary association groove 51 of the rear end cylinder 25A of the cannula 2A is housed in the rotary cylinder 52. The association claw 53 associatably associated with the rotary association groove 51 is provided at two facing places of the periphery of the rotary cylinder 52. The association claw 53 is rotated and associated with the periphery of the rotary cylinder 52 so as to come in and out a claw hole 53a provided aligning the rotary association groove 51 as shown in FIG. 8b. The association claw 53 is enforced by a spring 53b to keep the come-in state, namely the claw 53 is associated with the rotary association groove 51.

The numeral 54 shows a marker put where one association claw 53 of the rotary cylinder 52 is provided and shows a picturing tip position of the endoscope 3A. Therefore, it is convenient that the picturing top position of the endoscope 3A can be confirmed by seeing the marker 54.

The association groove 51 of the rear end cylinder 25A of the cannula 2A, the rotary cylinder 52 provided with association claws 53 of the endoscope 3A, and the cap nut 36 comprises the easy manual rotary association means.

FIG. 9a shows a laparoscope apparatus when the endoscope of FIG. 7 is inserted into the cannula of FIG. 6, FIG. 9b is a fragmental view taken in the direction of the arrow X3, and FIG. 9c is a view explaining the endoscope can be disassembled.

In FIG. 9a, the endoscope 3A is associated with the cannula 2A by easy manual operation by means of the association means 4, and the wide-angle lens 31a of the image picking-up means 31 at the tip of the endoscope 3A is provided close to the transparent member 24A or is provided so as to attach with the member 24A. The rotary association claw 53 of the rotary association means 5 is associated with the rotary association groove 51 so that the rotary position of the endoscope 3A and the cannula 2A is fixed.

When the association claw 53 is operated as shown in the outlined arrow in FIG. 9c, association is released so that the rotary position of the endoscope 3A and the cannula 2A can be changed, namely rotated, keeping the relative axial relation of the endoscope 3A and the cannula 2A by the association means 4 as shown in FIG. 9b. When operation of the association claw 53 is released at a desired position, it is associated with the rotary association groove 51 at the position and it keeps its rotary position.

According to the laparoscope apparatus 10A, rotary position of the endoscope 3A can be changed and locked against the cannula 2A, so that operation isn't hindered by the extended state of the connecting cable of the endoscope 3A by changing its rotary position, therefore improving operability.

The O-ring 45 provided at the base body 33A of the endoscope 3A is airtightly pressed on the auxiliary association hole 44 of the connection 26A airtightly inserted in the rear end cylinder 25A of the cannula 2A so that outer air is prevented from entering into the cannula 2A from the endoscope 3A side and condensation in the transparent member 24A at the tip of the cannula 2A because of moisture of outer air is prevented. Its condensation preventing effect is important because it is very difficult to wipe inside of the transparent member 24A.

FIG. 9c shows that the main body of the endoscope 3A can be disassembled from the rotary cylinder 52.

A female screw 36a is provided in the cap nut 36 and is associated with a male screw 52a provided for the rotary cylinder 52. A pair of positioning pins 33Ac are provided so as to face each other at the periphery of the guide cylinder part 33Aa of the base body 33A of the endoscope 3A. On the other hand, a positioning groove 52b is provided for the male screw 52a so as to be inserted with the positioning pins 33Ac.

The positioning groove 52b of the rotary cylinder is inserted into the positioning pins 33Ac of the rotary cylinder 52, the female screw 36a of the cap nut 36 is screwed to the male screw 52a of the rotary cylinder 52, the cap nut 36 is rotated to be fastened as far as possible in order to associate the base body 33A of the endoscope 3A and the rotary cylinder 52 by the cap nut 36. As the result, the rotary cylinder 52 is suitably aligned with the base body 33A of the endoscope 3A and the cylinder 52 is strongly fixed to the endoscope 3A so as to be worked together.

When the nut 36 is released and their association is released, the main body of the endoscope 3A comprised of the cap nut 36, the base body 33A, the connection cylinder 32 and the image picking-up means 31 can be extracted from the cannula 2A even if the rotary cylinder 52 is set for the cannula 2A.

The association means 41 keeps the relative axial position of the cannula 2A and the endoscope 3A, however, it doesn't constrain their reciprocal rotary position. Therefore, the endoscope 3A can be rotated against the cannula 2A only by means of the association means 41. However in such a case, an appropriate rotary position can't be fixed. Accordingly the easy manual rotary association means 5 can exert its effect because it can rotate the endoscope at a desired position and keep the position.

What is claimed is:

1. A laparoscope apparatus for use in laparoscopic surgery comprise:

a cannula with an inner hollow having therein a light guide means for introducing light to its tip end for illuminating an object to be observed, said cannula being airtightly sealed with transparent member at its tip end of said inner hollow; and an endoscope capable of being pulled into and out from said inner hollow of said cannula, said endoscope having therein an image pick-up means with a wide-angle lens, and said image pick-up means being disposed near to said transparent member in said cannula; and wherein:

said cannula further comprises an installation means bag an association hole into which said endoscope is inserted;

said endoscope is provided with a resiliently deformable fitting member, said fitting member being resiliently deformed so as to allow the detachment of said endoscope from said cannula, when said endoscope is pulled into and from said association hole of said installation means;

said cannula further comprises an installation means having plural association grooves and an association hole into which said endoscope is inserted; and said endoscope is attached with a fitting member with an association claw, said fitting member being constructed such that said association claw is engaged with any of said association grooves by inserting said endoscope attached with said fitting member into said association hole with said association claw opened and thereafter by closing said association claw.

2. The laparoscope apparatus as set forth in claim 1, wherein said light guide has a light emitting surface formed in such annular shape that it surrounds said transparent member and wherein an annular diffusion cover is further provided at a part of said cannula which touches said light emitting surface for outwardly diffusing light emitted from said emitting surface of said light guide in the peripheral direction.

3. The laparoscope apparatus as set forth in claim 1, wherein said light guide is constructed such that on its end side its annular diameter is gradually enlarged in the direction toward the front of said cannula.

4. The laparoscope apparatus as set forth in claim 2, wherein said annular diffusion cover is comprised of an annular concave lens.

5. The laparoscope apparatus as set forth in claim 1, wherein said light guide has a light emitting surface formed in such annular shape that it surrounds said transparent member and wherein an annular light guide prism is further provided at the end of inner hollow of said cannula for outwardly deflecting light emitted from said light emitting end surface of said light guide in its peripheral direction.

6. The laparoscope apparatus as set forth in claim 5, wherein said light deflecting prism has a light diffusion surface at least one end of either its incident or its emission end.

* * * * *